(12) United States Patent
Keady

(10) Patent No.: US 8,221,860 B2
(45) Date of Patent: *Jul. 17, 2012

(54) EARGUARD SEALING SYSTEM I: MULTI-CHAMBER SYSTEMS

(75) Inventor: John P. Keady, Boca Raton, FL (US)

(73) Assignee: Personics Holdings Inc., Boca Raton, FL (US)

( * ) Notice: Subject to any disclaimer, the term of this patent is extended or adjusted under 35 U.S.C. 154(b) by 1037 days.

This patent is subject to a terminal disclaimer.

(21) Appl. No.: 12/115,320

(22) Filed: May 5, 2008

(65) Prior Publication Data

US 2008/0299339 A1    Dec. 4, 2008

Related U.S. Application Data

(60) Provisional application No. 60/916,275, filed on May 4, 2007.

(51) Int. Cl.
*B32B 1/04* (2006.01)
*A61F 11/08* (2006.01)

(52) U.S. Cl. .................... 428/35.7; 181/135

(58) Field of Classification Search .............. 428/35.7, 428/34.1; 181/135
See application file for complete search history.

(56) References Cited

U.S. PATENT DOCUMENTS

| | | |
|---|---|---|
| 2,535,258 A | 12/1950 | Bland |
| 3,080,011 A * | 3/1963 | Henderson .................. 181/135 |
| 3,602,654 A | 8/1971 | Victoreen |
| 3,987,245 A | 10/1976 | Fasen |
| 4,732,930 A | 3/1988 | Tanaka |
| 4,741,344 A | 5/1988 | Danby et al. |
| 4,834,211 A | 5/1989 | Bibby et al. |
| 4,896,679 A | 1/1990 | St. Pierre |
| 4,962,537 A | 10/1990 | Basel et al. |
| 5,213,580 A | 5/1993 | Slepian |
| 5,252,318 A | 10/1993 | Joshi |
| 5,256,765 A | 10/1993 | Leong |
| 5,333,622 A | 8/1994 | Casali et al. |
| 5,410,016 A | 4/1995 | Hubbell |
| 5,483,027 A | 1/1996 | Krause |
| 5,514,379 A | 5/1996 | Weissleder |
| 5,525,334 A | 6/1996 | Ito |
| 5,575,815 A | 11/1996 | Slepian |
| 5,589,568 A | 12/1996 | Higashijima |
| 5,634,946 A | 6/1997 | Slepian |
| 5,662,609 A | 9/1997 | Slepian |
| 5,674,287 A | 10/1997 | Slepian |
| 5,695,480 A | 12/1997 | Evans |
| 5,702,361 A | 12/1997 | Evans |
| 5,749,922 A | 5/1998 | Slepian |
| 5,766,704 A | 6/1998 | Allen |
| 5,843,156 A | 12/1998 | Slepian |
| 5,858,746 A | 1/1999 | Hubbell |
| 5,876,741 A | 3/1999 | Ron |

(Continued)

*Primary Examiner* — Rena Dye
*Assistant Examiner* — Erik Kashnikow
(74) *Attorney, Agent, or Firm* — RatnerPrestia

(57) ABSTRACT

Multi-chamber coatings are provided. The multi-chamber coating includes a first medium and a second medium. The first medium covers at least a first portion of the second medium so as to form first and second chambers. At least one material property of the first medium is different than the second medium. The first chamber and the second chamber share a wall. The wall is configured to apply a restorative force upon deformation of the first or second chambers. The coating is configured to be attached to an object that is configured to be inserted into an orifice.

19 Claims, 6 Drawing Sheets

U.S. PATENT DOCUMENTS

| | | | |
|---|---|---|---|
| 5,939,485 | A | 8/1999 | Bromberg |
| 5,942,209 | A | 8/1999 | Leavitt |
| 5,976,648 | A | 11/1999 | Li |
| 6,090,911 | A | 7/2000 | Petka |
| 6,094,494 | A | 7/2000 | Haroldson |
| 6,113,629 | A | 9/2000 | Ken |
| 6,256,396 | B1 | 7/2001 | Cushman |
| 6,339,648 | B1 | 1/2002 | McIntosh et al. |
| 6,393,130 | B1 | 5/2002 | Stonikas et al. |
| 6,451,429 | B2 | 9/2002 | Mumick |
| 6,532,682 | B2 | 3/2003 | Futschik |
| 6,660,247 | B1 | 12/2003 | Gutowska |
| 6,671,381 | B1 | 12/2003 | Lux-Wellenhof |
| 6,695,093 | B1 | 2/2004 | Falco |
| 6,731,772 | B1 * | 5/2004 | Byun ............................ 381/380 |
| 7,130,437 | B2 | 10/2006 | Stonikas et al. |
| 7,164,775 | B2 | 1/2007 | Meyer et al. |
| 7,227,968 | B2 | 6/2007 | van Halteren et al. |
| 7,362,875 | B2 | 4/2008 | Saxton et al. |
| 7,387,187 | B2 | 6/2008 | Widmer et al. |
| 2002/0153192 | A1 | 10/2002 | Falco et al. |
| 2002/0168319 | A1 | 11/2002 | Filler |
| 2004/0165742 | A1 * | 8/2004 | Shennib et al. ............... 381/326 |
| 2006/0081415 | A1 | 4/2006 | Knauer et al. |
| 2006/0159298 | A1 | 7/2006 | von Dombrowski et al. |
| 2007/0116319 | A1 | 5/2007 | Hagberg |
| 2008/0144871 | A1 | 6/2008 | Purcell et al. |
| 2009/0103763 | A1 * | 4/2009 | Petef et al. .................... 381/380 |
| 2009/0173353 | A1 | 7/2009 | Purcell et al. |
| 2009/0320858 | A1 | 12/2009 | Purcell et al. |
| 2009/0320859 | A1 | 12/2009 | Purcell et al. |

* cited by examiner

EARGUARD SEALING SYSTEM I: MULTI-CHAMBER SYSTEMS

CROSS-REFERENCE TO RELATED APPLICATIONS

This application claims the benefit of U.S. provisional patent application No. 60/916,275 filed on 4 May 2007. The disclosure of which is incorporated herein by reference in its entirety.

FIELD OF THE INVENTION

The present invention relates to chambered material configuration useable in orifices or as coatings for objects to be inserted into orifices, and more particularly though not exclusively for chambered material configurations used in organic orifices.

BACKGROUND OF THE INVENTION

Various methods of sealing an orifice, or coating a device to insert into an orifice (organic and non-organic) have been developed. Generally the coatings and sealing mechanism use simple flanges, single layer coatings, or layered coatings. All have various disadvantages in tactile response, comfort, and sealing ability.

SUMMARY OF THE INVENTION

At least one exemplary embodiment is directed to a multi-chamber coating comprising: a first medium; and a second medium, where the first medium covers at least a first portion of the second medium so as to form first and second chambers, where at least one material property of the first medium is different than the second medium, where the first chamber and the second chamber share a wall, where the wall is configured to apply a restorative force upon deformation of the first or second chamber, where the first and second chambers form at least a portion of a coating, and where the coating is configured to be attached to an object that is configured to be inserted into an orifice.

A sealing section comprising: a central core; and a multi-chamber coating, where the multi-chamber coating is attached to the central core forming a sealing section, where the sealing section's length is less than 30 mm, and where the largest diameter along the sealing section's length is less than 20 mm, where the coating comprises: a first medium; and a second medium, where the first medium covers at least a first portion of the second medium so as to form first and second chambers, where at least one material property of the first medium is different than the second medium, where the first chamber and the second chamber share a wall, where the wall is configured to apply a restorative force upon deformation of the first or second chamber, where the first and second chambers form at least a portion of a coating.

Further areas of applicability of exemplary embodiments of the present invention will become apparent from the detailed description provided hereinafter. It should be understood that the detailed description and specific examples, while indicating exemplary embodiments of the invention, are intended for purposes of illustration only and are not intended to limit the scope of the invention.

BRIEF DESCRIPTION OF THE DRAWINGS

Exemplary embodiments of the present invention will become more fully understood from the detailed description and the accompanying drawings, wherein.

DETAILED DESCRIPTION OF EXEMPLARY EMBODIMENTS OF THE PRESENT INVENTION

Figure 1:
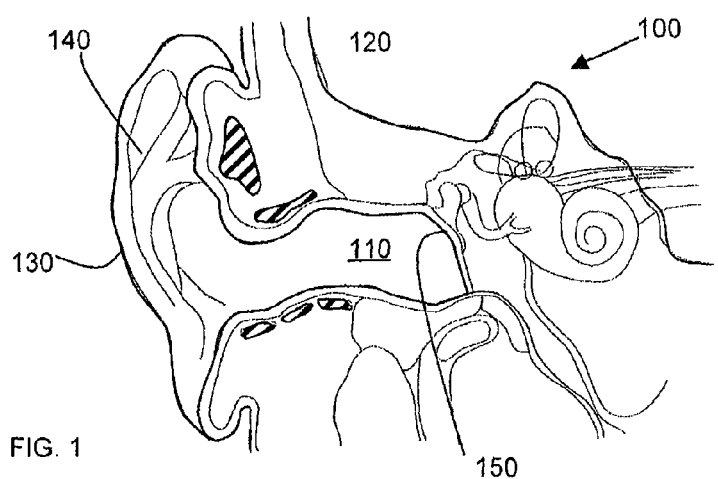
FIG. 1 illustrates an example of an orifice (e.g., ear)

The following description of exemplary embodiment(s) is merely illustrative in nature and is in no way intended to limit the invention, its application, or uses.

Exemplary embodiments are directed to or can be operatively used on various wired or wireless earpieces devices (e.g., earbuds, headphones, ear terminal, behind the ear devices or other acoustic devices as known by one of ordinary skill, and equivalents).

Note that medium can refer to any medium mentioned below and its equivalent as well as fluids (air, liquid, foams, gels, solids, electro active polymers and other materials as known by one of ordinary skill in the arts that can be used in coatings and fillers). Additionally the coatings can be used on any object not just those inserted into orifices (e.g., ear canals, blood vessels, pipes, irregular shaped cross-sectional openings, non-circular cross sectional openings).

Processes, techniques, apparatus, and materials as known by one of ordinary skill in the art may not be discussed in detail but are intended to be part of the enabling description where appropriate. For example specific computer code may not be listed for achieving each of the steps discussed, however one of ordinary skill would be able, without undo experimentation, to write such code given the enabling disclosure herein. Such code is intended to fall within the scope of at least one exemplary embodiment.

Additionally exemplary embodiments are not limited to earpieces, for example some functionality can be implemented on other systems with speakers and/or microphones for example computer systems, PDAs, Blackberry™ Smartphones, cell and mobile phones, and any other device that emits or measures acoustic energy. Additionally, exemplary embodiments can be used with digital and non-digital acoustic systems. Additionally various receivers and microphones can be used, for example MEMs transducers, diaphragm transducers, for example Knowles' FG and EG series transducers.

Notice that similar reference numerals and letters refer to similar items in the following figures, and thus once an item is defined in one figure, it may not be discussed or further defined in the following figures.

Additionally, the size of structures used in exemplary embodiments are not limited by any discussion herein (e.g., the sizes of structures can be macro (centimeter, meter size), micro (micro meter), nanometer size and smaller).

Various materials are useable in exemplary embodiments. For example material referred to herein can be viscous and can include silicone-based polymers, gels, vinyl elastomers, or any other material of sufficient properties to allow the deformation of a membrane cavity from user contact. Materials can also be used to provide a slow reformation of the original membrane cavity shape after it has been deformed and released. In this regard, a silicone gel or other non-cross-linked polymer or uncatalyzed materials can be used. It should be appreciated that the composition of the fillable (e.g., material used in the cavity or chamber) material could be altered for applications in which varied membrane characteristics are desired (i.e. more stiffness, durability, more or less deformability and/or longer-lasting deformation). The fillable material may be elastically deformed or it may be deformed by displacement, which is the actual movement or flow of the fillable material in response to pressure, such as that from a user's fingertips. In addition, the fillable material could be altered for applications in which varied temperature conditions would be encountered during the use of particular products on which the membrane cavity is mounted.

Membranes can be made of any material, rigid or elastic, including various plastic or metal materials, or it can be made of a membrane formed of thin rubber-based material, deformable plastic or silicone-based materials or other elastomeric materials suitable for a given application. If the base is configured as a flexible membrane, the cavity (e.g., chamber covered by an outer membrane) can more easily conform to a product's surface, thereby increasing the ease with which the cavity can be installed, removed, and replaced. Likewise, the outer membrane also can be made of a thin rubber-based material, deformable plastic or silicone polymer materials, or other elastomeric materials suitable for a given application. If the base membrane and outer membrane are made of silicone material, both should be from 0.50 mm to 2.5 mm in thickness. In this regard, the base may be a membrane instead of a piece of rigid material. The edges of the outer membrane and the base membrane can be mechanically fastened or clamped forming the membrane cavity. Additionally at least a portion of the base membrane can be adhesively attached (e.g., adhesive tape, glue) or mechanically fastened to the support structure.

In applications where the base membrane is attached to the support structure via an adhesive, various types of adhesives can be used depending on the type of product surface (i.e., support structure) and the type of base material used. For example, if the base membrane of the cavity is a silicone polymer, then cyanoacrylate glue or 3M Super Silicone brand sealant can be used. In another example, if the support structure is a thermoplastic material and the base membrane of the cavity is a polyethylene plastic material, then cyanoacrylate glue or 3M Super Silicone brand sealant can be used.

One type of adhesive that may be used is 3M brand Super silicone sealant, which is a one-component, paste-like material that cures to a tough, elastomeric solid when exposed to atmospheric moisture. This sealant will adhere to clean, bare, or painted metal, glass, non-oily wood, abraded rubber and many types of plastics. The sealant is a one-part vulcanizing silicone rubber type having the consistency of a non-sagging paste. It is made of 100% solids and has a net weight of approximately 8.3-8.7 pounds per gallon. This sealant is available in clear, white or black colors. The sealant can be extruded from an 0.125 inch orifice using a pressure of ninety pounds per square inch. Such extrusion results in a flow of approximately 350 gallons per minute.

The silicone sealant can be an acetoxy cure type. In particular, upon exposure to moisture, the silicone sealant will give off small amounts of acetic acid while the sealant cures. It is not recommended that the acetic acid vapors be inhaled. The sealant will cure in 24 hours and has a tack free time of 10-20 minutes at 77.degree. F. (25.degree. C.) with 50% relative humidity. The sealant's tensile strength is approximately 350 psi, its elongation property is 450%, and its hardness is approximately 25-30 Shore A. The sealant has temperature stability from −85.degree. F. to 450.degree. F. (−65.degree. C. to 232.degree. C.) and can withstand intermittent exposure to temperatures as high as 500.degree. F. (280.degree. C.). The sealant is believed to have good resistance to various weathering conditions, including UV radiation, rain, snow, etc, without hardening, cracking, or shrinking.

For optimum adhesion with the above adhesive, the support structure and the lower surface of the base membrane should be clean, dry, and free from oil, grease or other foreign material. If necessary, metal surfaces should be wiped with a non-oily solvent. Rubber surfaces should be abraded to promote adhesion. Depending on environmental conditions, the base and product surface should be joined within 5-10 minutes, before the tack-free time of the sealant passes.

Additional materials that can be used include more exotic materials, for example materials that are electro active. The sealing section (e.g., which can include the coating) can use various materials (e.g., viscosity varying polymers), for example polymers that are liquid at one temperature then gel at another, or switch between a gel and liquid with pH, current, pressure, or any other variation in energy, or any other similar material as known by one of ordinary skill in the relevant arts. For example the following is a non-limiting list of references that discuss materials that can be used: U.S. Pub. No. 2002/0168319; U.S. Pat. No. 6,660,247; U.S. Pat. No. 6,352,682; U.S. Pat. No. 6,113,629; U.S. Pat. No. 6,090,911; U.S. Pat. No. 5,976,648; U.S. Pat. No. 5,942,209; U.S. Pat. No. 5,939,485; U.S. Pat. No. 5,876,741; U.S. Pat. No. 5,858,746; U.S. Pat. No. 5,843,156; U.S. Pat. No. 5,766,704; U.S. Pat. No. 5,749,922; U.S. Pat. No. 5,702,361; U.S. Pat. No. 5,695,480; U.S. Pat. No. 5,674,287; U.S. Pat. No. 5,662,609; U.S. Pat. No. 5,634,946; U.S. Pat. No. 5,589,568; U.S. Pat. No. 5,575,815; U.S. Pat. No. 5,525,334; U.S. Pat. No. 5,514,379; U.S. Pat. No. 5,410,016; U.S. Pat. No. 5,256,765; U.S. Pat. No. 5,252,318; U.S. Pat. No. 5,213,580; U.S. Pat. No. 6,660,247; and U.S. Pat. No. 4,732,930. Additionally electro-active polymers can be utilized. For example gels that expand and contract when an electric field is applied, likewise materials can bend and deform when voltage is applied across its surface.

The device can include a sealing section having a coating, that can be made of various materials, for example viscosity variable polymers, or temperature variable viscosity materials. As the device is inserted into an orifice (e.g., ear, mouth, anus, nose, artery, vein) a resistance force can be encountered by a portion of the sealing section. The force can act as an energy variation event which can change the physical properties, for example liquefies (e.g., lowers the viscosity, could still be gel like) the fillable material allowing easy flow or deforms a deformable sealing section. As the impulse forces stop and stability sets in (net equilibrium force reduced) the portion of the sealing section that liquefied in response to a force gellifies seating the device. Note that a sealing section could be a chamber coating.

Note that in some materials there is a phase shift in the temporal response of the medium. For example when a force is applied there may be a 10 msec delay in the liquefaction (change in viscosity) of the sealing element's fillable material. For example U.S. Pat. No. 6,451,429 discusses a method to synthesize a temperature sensitive polymer, NiPAm polymers. U.S. Pat. No. 6,451,429 discusses a condensation reaction of an intermediate salt to form homopolymers, copolymers and terpolymers of N-isopropyl acrylamide (NiPAm) with acrylic acid and/or alkyl acrylates in a molten state, which is adaptable to a continuous reactive extrusion process. Binder compositions, water-dispersible products and thermoformable articles containing the NiPAm polymers are also disclosed. Additional non-limiting examples are pH/temperature sensitive linear terpolymers (poly(N-isopropylacrylamide-co-butylmethacrylate-co-acrylic acid)).

Note that various materials have been discussed, in addition all forms of electroactive polymers can be used. For example electroactive polymers (EAPs) are touted as the basis for future artificial muscles. EAPs can be deformed repetitively by applying external voltage across the EAP, and they can quickly recover their original configuration upon reversing the polarity of the applied voltage. Some EAPs have a high load bearing capacity to mass ratio, short response time, and nearly linear deformation response with respect to applied voltage. Artificial muscle polymers can be formed from a conductive polymer doped with surfactant molecule or from an ionic polymer metal composite (IPMC). Doped electroactive polymers (EAPs) are conductive polymers (e.g., polypyrrole or polyanaline) doped with a surfactant (e.g., sodium dodecyl benzene sulfonate). IPMCs typically consist of perfluorsulfonate polymers that contain small proportions of sulfonic or carboxylc ionic functional groups. Nafion®, a polymer made by DuPont, is one example of a poly(tetrafluoroethylene) based ionomer. The outer surface region (less than a micrometer) of the polymer sheet is then impregnated with a conductive metal such as platinum or gold. The resulting EAP polymer can absorb water until its physical ability to expand is balanced by the affinity of water for the polymer-fixed ions and free counter ions. When an electrical field is applied across the EAP, the EAP deforms as a result of stresses generated by the movement of water and mobile positive ions in the polymer composite.

FIG. 1 illustrates the general physical arrangement of the ear region 100, including a pinna 130, ridge 140, outer ear region 120, inner ear canal (IEC) region 110 and the eardrum 150. At least one exemplary embodiment is related to an earphone inserted into the ear canal, where a portion of a sealant section acoustically seals an inner ear canal region 110.

Figure 2:
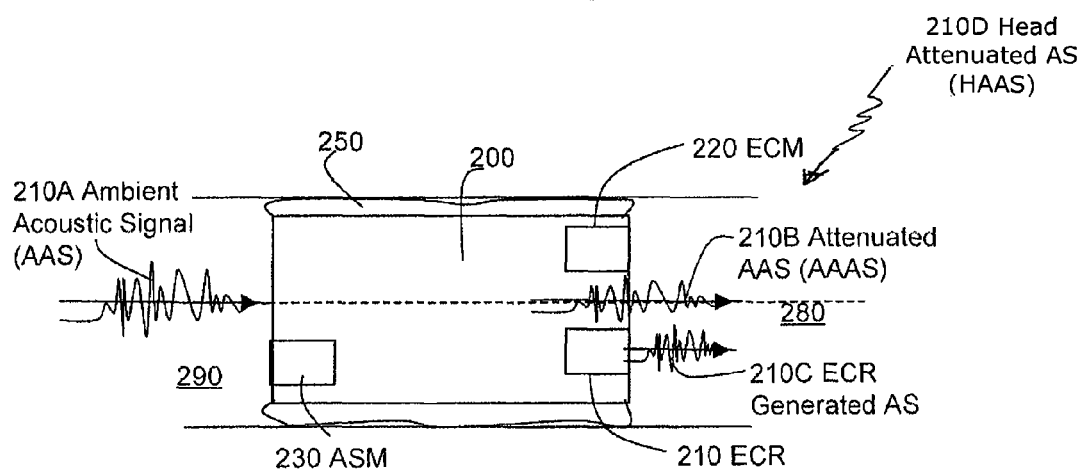
FIG. 2 illustrates an example of an object to insert into an orifice.

FIG. 2 illustrates a generalized version of an earpiece 200 and some associated parts (e.g., 230, 220, and 210) in an ear canal (EC) (an example of an orifice), which is a non limiting example of at least one orifice device (e.g., earpiece) which can contain a coating and/or layer 250 in accordance to at least one exemplary embodiment. When inserted the earpiece 200 generally defines the two regions 290 and 280. Through the earpiece 200 there is some attenuation. For example, an ambient acoustic signal (AAS) 210A, will travel through the earpiece 200 and/or via bone conduction (not shown) and be attenuated forming an attenuated ambient acoustic signal (AAAS) 210B. The AAAS 210B then travels to the eardrum (ED). The other additional acoustic signal 210C (e.g., the ECR generated AS or ECRAS), which can travel to the eardrum, can be generated by the ear canal receiver (ECR) 210. Thus the total AS imparting energy upon the ED can be due to the AAAS 210B (which can include a bone conduction part not in the IEC region 280) and the ECRAS 210C. Various combinations of elements (e.g., parts) can be used in exemplary embodiments such as the ECR 210 (e.g., Knowles FG3629), the ear canal microphone (ECM) 220 (e.g., Knowles FK3451), and the ambient signal microphone (ASM) 230 (e.g., Knowles FG3629). Note that ECM 220 can also measure head attenuated acoustic signals (HAAS) 210D, which for example could originate from voice.

During operation, a personal audio device outputs a driving signal to ECR 210 so that ECR 210 outputs an acoustic signal 210C. Similarly, ASM 230 converts the ambient environment noise into an environmental noise signal, which is input to ECR 210 to generate an ECR ambient sound acoustic signal, which could make up a part of acoustic signal 210C. ECM 220 receives an ambient acoustic signal AAS210B and the ECR-generated signal 210C and converts it into a total acoustic sound signal to be operated on by earpiece 200 as discussed below.

Figure 3:
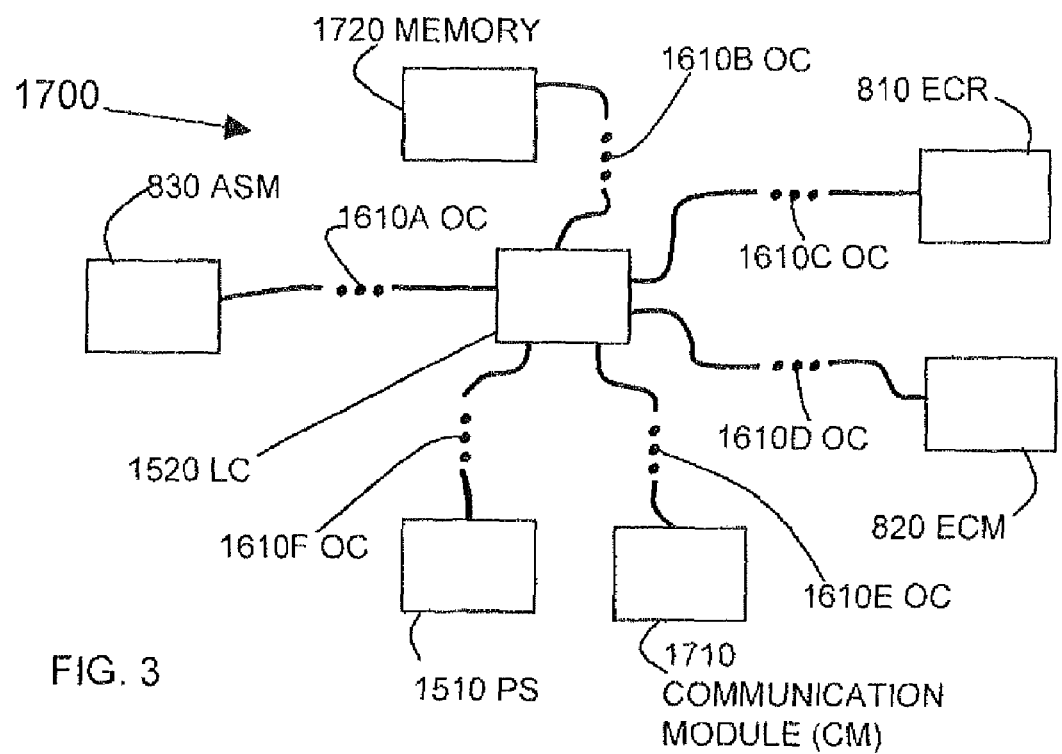
FIG. 3 illustrates a general configuration of electronic elements in an earpiece.

FIG. 3 illustrates a self-contained version of an earpiece 1700 according to at least one exemplary embodiment, including a power source (PS) 1510 (e.g., zinc-air battery (ZeniPower A675P), Li-ion battery), and a logic circuit (LC, e.g., Gennum Chip GA3280) 1520 in addition to ECR 810. Earpiece 1700 can also include a wireless module for wireless communications (not shown) or can be wired. Earpiece 1700 can also connect remotely to various parts (e.g., via a wired or wireless connection). As illustrated the LC 1520 and PS 1510 are operatively connected (OC) 1610 (e.g., via a wire or wirelessly) to the earpiece 1700. For example earpiece 1700 can be an earbud that includes ECR 810, whose signals travel back and forth via a wire that is operatively connected via a wire to LC 1520, which in turn can be operatively connected to PS 1510. Note that ECR 810 can also be a dual purpose ECR/ECM, where when the receiver function (ECR mode) is not used the microphone function (ECM mode) can be used. For example U.S. Pat. No. 3,987,245 discusses a dual-purpose transducer that can be used as a microphone and/or a receiver. Logic circuit 1520 has an operative connection 1610A to ASM 830; an operative connection 1610B to a memory 1720; an operative connection 1610C to ECR 810; an operative connection 1610D to ECM 820; an operative connection (e.g., operatively connected) 1610E to a communication module 1710; and an operative connection 1610F to a power source 1510. Again, it should be noted that the operative connection could be either wireless or hard wired and that as discussed above, elements other than ECR 810 could be remote from earpiece 1700. It should be understood that ASM 830 should not be too remote from the ear of the user in order to properly measure the ambient sound and ambient environment.

Figure 4:
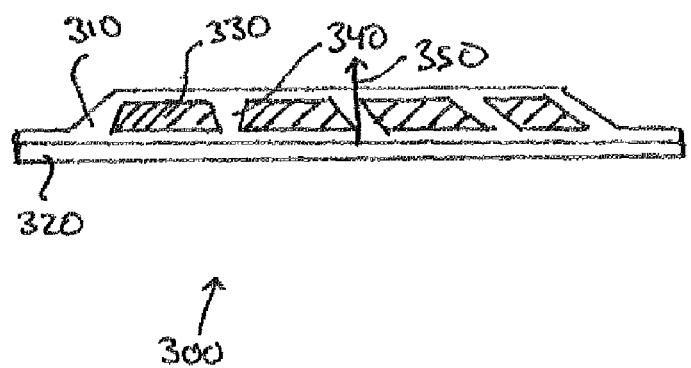
FIG. 4 illustrates at least one exemplary embodiment of a coating.

FIG. 4 illustrates a coating 300 in accordance with at least one exemplary embodiment, including an outer membrane 310 (first medium), a base membrane 320, a cavity (e.g. chamber) filled with a filler material 330 (second medium), and walls 340. Where when the coating is deformed the walls 340 aid to place vertical and horizontal forces 350 in opposition to the deformation.

Figure 5A:
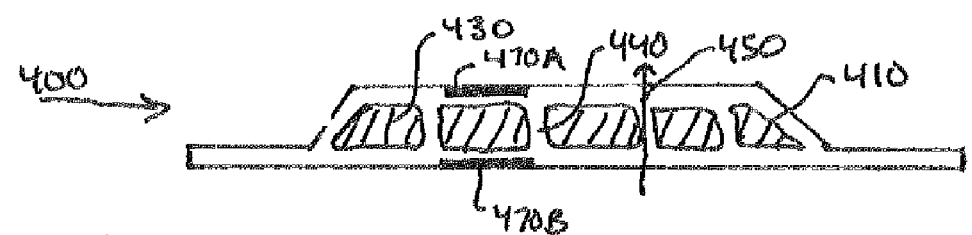
FIGS. 5A, 5B, 5C, and 5D illustrate various examples of exemplary embodiments of coating or the use of coatings in accordance with the present invention.

FIG. 5A illustrates a coating 400 in accordance with at least one exemplary embodiment, including a single membrane 410, having cavities 430 filled with a filler material, where the cavities 430 have vertical walls 440. Where when the coating is deformed the walls 440 aid to place vertical and horizontal forces 450 in opposition to the deformation. In at least one exemplary embodiment the chambers (e.g., cavities) 430 can be filled with electro active polymers (e.g., electro expansive and/or contractive gel), with a set of electrodes 470A and 470B.

Figure 5B:
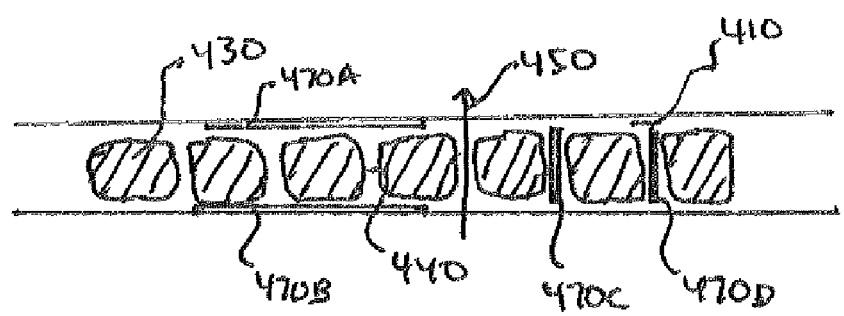

FIG. 5B illustrates another configuration of 400 where the electrodes can be vertically inclined 470C and 470D.

Figure 5C:
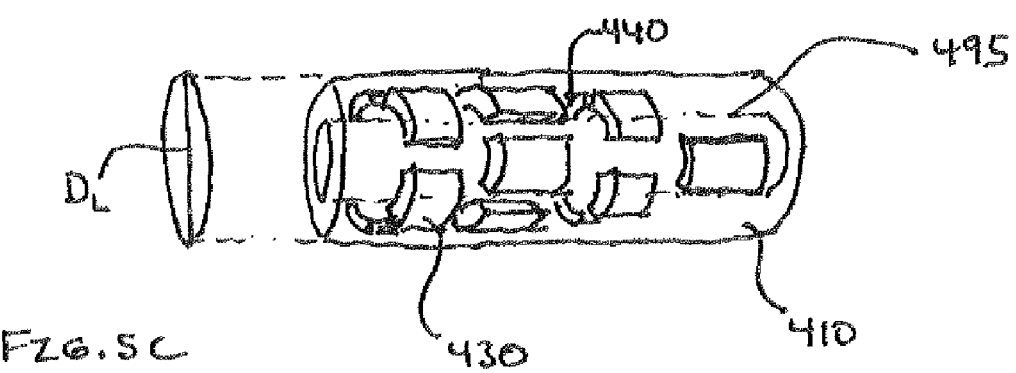

FIG. 5C illustrates an object including a core 495, surrounded by a coating comprising a chamber 430, wall structure 440, and a surrounding medium 410, where the chamber 430 can be repeated or copied over an angular extend about the core 495. Note that the cross section can be non-circular, for example square, irregular, ellipsoidal, and can have a largest diameter of $D_L$.

Figure 5D:
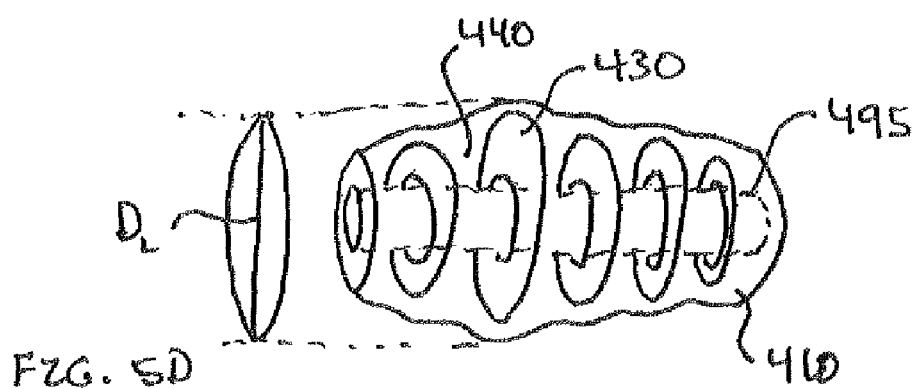

FIG. 5D illustrates an object including a core 495, surrounded by a coating comprising a chamber 430, wall structure 440, and a surrounding medium 410, where the chamber 430 can be repeated or copied over an angular extend about the core 495. Note that the cross section can be non-circular, for example square, irregular, ellipsoidal, and can have a largest diameter of $D_L$.

Note that similar to the configuration illustrated in FIGS. 5A and 5B, electrodes (e.g., ring electrodes, or cylindrical electrodes) can be placed about the core to effect the chambers 430 if filled with electro responsive material for example electro active polymers.

Figure 6A:
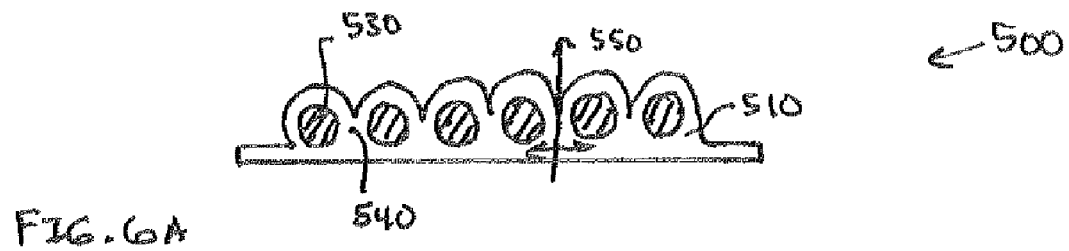
FIGS. 6A and 6B illustrate various examples of exemplary embodiments of coating or the use of coatings in accordance with the present invention.

FIG. 6A illustrates a coating 500 in accordance with at least one exemplary embodiment, including a single membrane 510 (which can optionally be attached to a base membrane, not shown) (note in the exemplary embodiments the base membranes discussed herein can be attached to a support structure of a device or object (e.g., earphone) or the base membrane can be a surface of the support structure), having cavities 530 filled with a filler material, where the cavities 530 have a shaped cross section (e.g., circular, triangular, square, irregular) separated by walls 540. Where when the coating 500 is deformed the walls 540 aid to place vertical and horizontal forces 550 in opposition to the deformation.

Figure 6B:
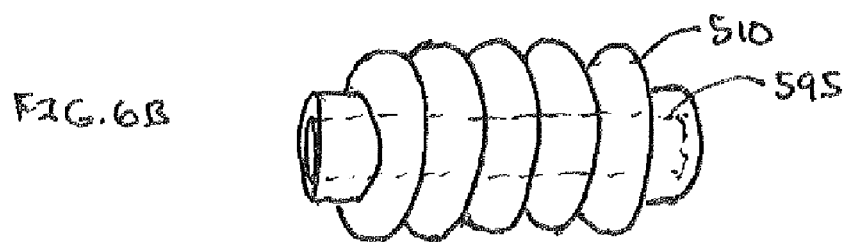

FIG. 6B illustrates an object having a coating similar to that illustrated in FIG. 6A surrounding a core 595.

Figure 7:
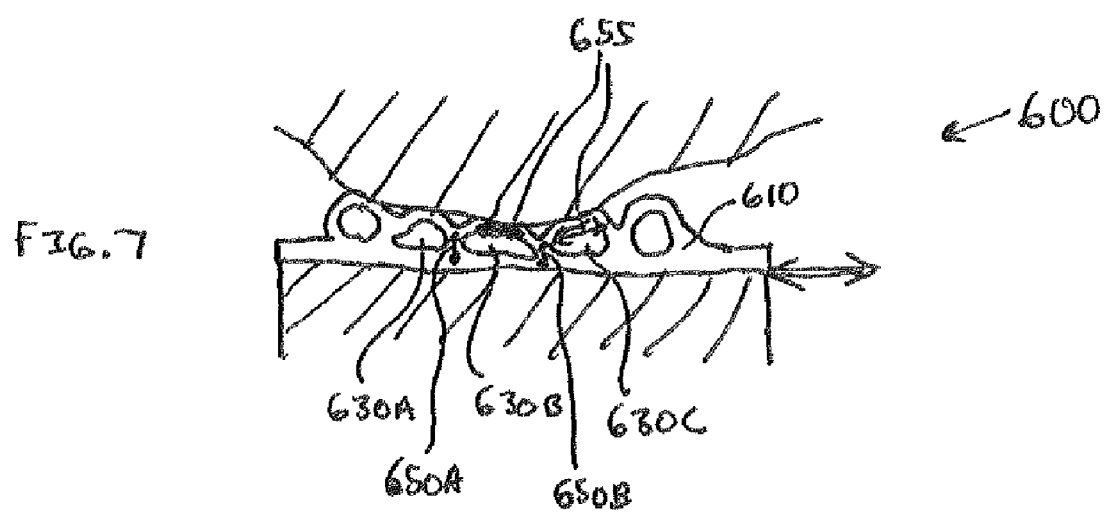
FIG. 7 illustrates the insertion of the coating illustrated in FIG. 6A into an orifice and its interaction with the wall of the orifice.

FIG. 7 illustrates the exemplary embodiment illustrated in FIG. 6A of an object 600 having a coating inserted into an orifice (e.g., ear canal) where the center cavities (630A, 630B, 630C) are deformed, pressing back against the ear canal wall via vertical forces 650A and 650B and horizontal forces 655.

Figure 8:
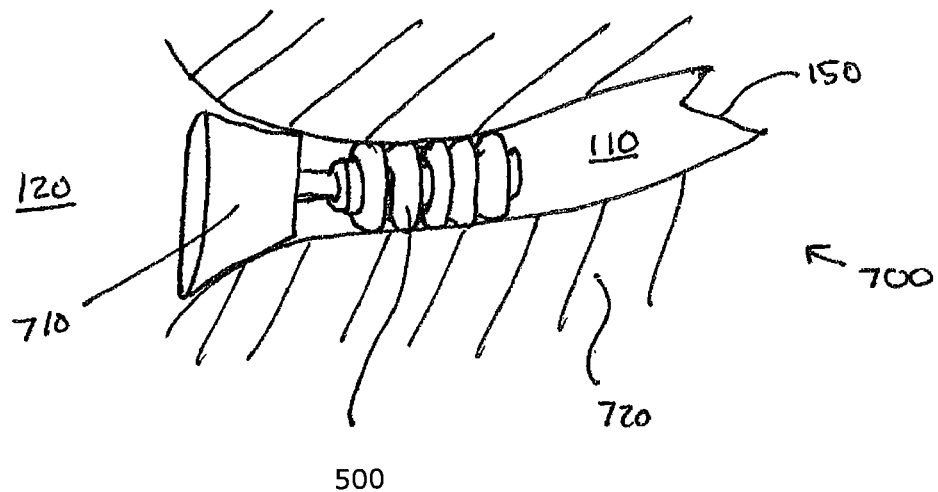
FIG. 8 illustrates the insertion of an object including a coating forming a sealing section into an orifice.

FIG. 8 illustrates an earpiece 700 with the coating 500 with cylindrical cavities as illustrated in FIG. 6A operatively attached to the core of an earpiece support structure 710, inserted into an ear canal, where deformation of the coating against the ear canal walls 720 results in an acoustically sealed inner ear canal region 110 from the ambient environment 120, so that acoustic energy from the ambient environment is reduced before impinging the ear drum 150.

Figure 9:
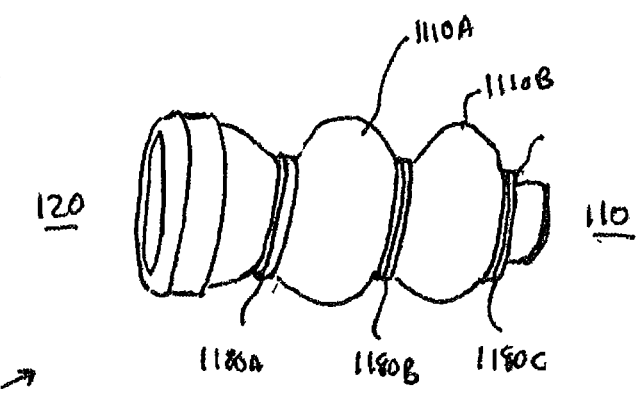
FIG. 9 illustrates another object having sealing sections which include coatings.

FIG. 9 illustrates multiple coatings 1110A, and 1110B separated by various fasteners 1180A, 1180B, and 1180C, where the multiple coatings can acoustically seal the earpiece 1100 into an ear canal.

Figure 10:
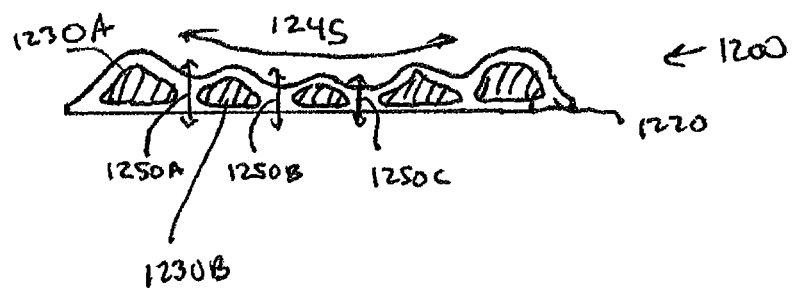
FIGS. 10 and 11 illustrate two coatings in accordance with at least two exemplary embodiments.
Figure 11:
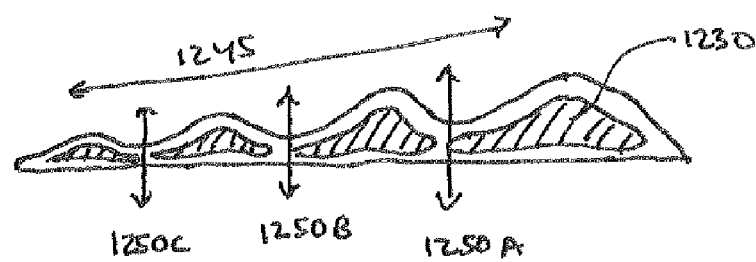

FIGS. 10 and 11 illustrate various configurations of coating 1200 where the chambers 1230 (and 1230A and 1230B in FIG. 10) can vary in size from one end to another so as to generate a curvature or slanting or other curve or line 1245. The walls 1250A, 1250B, and 1250C can exert a restoring force when the chambers are deformed, where the restoring force can vary depending upon the geometry of the walls (e.g., thickness of the walls)

At least one exemplary embodiment is directed to a multi-chamber coating comprising: a first medium; and a second medium, where the first medium covers at least a first portion of second medium so as to form a first and second chamber, where at least one material property of the first medium is different than the second medium, where the first chamber and second chamber share a wall, where the wall is configured to apply a restorative force upon deformation of the first or second chamber, where the first and second chamber form at least a portion of a coating, and where the coating is configured to be attached to an object that is configured to be inserted into an orifice. For example FIG. 10 illustrates a first medium 1220, and a second medium 1230A and 1230B forming chambers. The first medium can be of higher durometer than the second medium or vice versa. The object in this non limiting example can be the core of an earpiece or a tube that is inserted into other orifices.

In at least one exemplary embodiment a third medium, for example in 1230B can have different properties than the second medium in 1230A. For example the third medium can be a thermal responsive polymer (e.g., gel) or an electro active polymer. In at least one exemplary embodiment the properties (durometer, state, viscosity, color) of the third medium can change with energy variation (e.g., energy input or sink) (e.g., temperature change).

At least one exemplary embodiment is directed to a sealing section of an object where the sealing section comprises: a central core (e.g., a central tube portion of an earpiece (an example of an object)); and a multi-chamber coating (e.g., concentric tubes of a second medium surrounded by a first medium), where the multi-chamber coating is attached to the central core forming a sealing section, where the sealing section's length is less than a chosen amount to fill a portion of the orifice (e.g., for an ear canal, 30 mm), and where the largest diameter along the sealing sections length is less than a chosen amount to seal the orifice (e.g., for an ear canal 20 mm), where the coating comprises: the first medium; and the second medium, where the first medium covers at least a first portion of the second medium so as to form first and second chambers, where at least one material property of the first medium is different than the second medium, where the first chamber and the second chamber share a wall, where the wall is configured to apply a restorative force upon deformation of the first or second chamber, where the first and second chambers form at least a portion of a coating. Note that the dimensions can vary, for example when the object to be attached is to be inserted into a blood vessel or a pipe.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 90 degrees) should be interpreted to be "about" the value of the stated number (e.g., about 90 degrees).

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. A multi-chamber coating of an object configured to be inserted into an ear canal, the multi-chamber coating comprising:

a first medium having a plurality of chambers, the plurality of chambers separated from each other by respective walls of the first medium, the plurality of chambers being arranged along a length of the object to be at different depths of the ear canal when inserted into the ear canal; and a second medium disposed in the plurality of chambers, at least one material property of the first medium being different than the second medium, where the second medium is configured to be deformed by a surface of the ear canal contacting the multi-chamber coating, and the walls of the first medium are configured to apply a restorative force to the surface of the ear canal responsive to the second medium being deformed.

2. The coating according to claim 1, where the coating includes at least one further chamber and a third medium disposed in the at least one further chamber and there is at least one different material property between the second medium and the third medium.

3. The coating according to claim 1, where the second medium includes a thermally responsive polymer.

4. The coating according to claim 1, where the first medium includes a thermally responsive polymer.

5. The coating according to claim 1, where the first medium includes an electro active polymer.

6. The coating according to claim 1, where the second medium includes an electro active polymer.

7. The coating according to claim 1, where the plurality of chambers have substantially a same dimension.

8. The coating according to claim 1, where the plurality of chambers are symmetrically arranged about a central axis extending along the length of the object.

9. The coating according to claim 2 where the third medium includes an electro active polymer.

10. The coating according to claim 1, where the plurality of chambers have different dimensions.

11. The coating according to claim 1, where each chamber includes at least one of a circular cross-section, a triangular cross-section, a rectangular cross-section or a polygonal cross-section.

12. The coating according to claim 1, where the plurality of chambers include annular rings disposed along the length of the object.

13. The coating according to claim 1, where at least one of the chambers includes an arc segment extending around a portion of a perimeter of the object.

14. The coating according to claim 1, where the plurality of chambers are asymmetrically arranged about a central axis extending along the length of the object.

15. A sealing section configured to be inserted into an ear canal comprising:

a central core having a length and a central axis along the length of the central core; and a multi-chamber coating attached to the central core and disposed along the length of the central core where the multi-chamber coating comprises:

a first medium having a plurality of chambers, the plurality of chambers separated from each other by respective walls of the first medium, the plurality of chambers being arranged along the length of the central core to be at different depths of the ear canal when inserted into the ear canal; and a second medium disposed in the plurality of chambers, at least one material property of the first medium being different than the second medium, where the second medium is configured to be deformed by a surface of the ear canal contacting the multi-chamber coating, and the walls of the first medium are configured to apply a restorative force to the surface of the ear canal responsive to the second medium being deformed.

16. The sealing section according to claim 15, where the plurality of chambers include annular rings disposed along the length of the central core.

17. The sealing section according to claim 15, where at least one of the chambers includes an arc segment extending around a portion of a perimeter of the central core.

18. The sealing section according to claim 15, where the plurality of chambers are symmetrically arranged about the central axis.

19. The sealing section according to claim 15, where the plurality of chambers are asymmetrically arranged about the central axis.

* * * * *